United States Patent [19]

Stevens

[11] Patent Number: 5,322,253
[45] Date of Patent: Jun. 21, 1994

[54] UNIVERSAL I.V. STAND MOUNTING SYSTEM

[75] Inventor: Brian Stevens, Provo, Utah

[73] Assignee: Merit Medical Systems, Inc., Salt Lake City, Utah

[21] Appl. No.: 984,458

[22] Filed: Dec. 2, 1992

[51] Int. Cl.⁵ ............................................. A47B 96/07
[52] U.S. Cl. .................................... 248/229; 248/125; 248/231.7
[58] Field of Search ............... 248/125, 229, 231.7, 248/291

[56] References Cited

U.S. PATENT DOCUMENTS

| | | | |
|---|---|---|---|
| 2,063,924 | 12/1936 | Hanko | 24/81 |
| 2,269,790 | 1/1942 | Sherrill | 248/229 X |
| 2,876,027 | 3/1959 | Sulmonetti | 248/229 X |
| 3,295,812 | 1/1967 | Schneider et al. | 248/229 |
| 3,544,060 | 12/1970 | Stoltz | 251/9 |
| 3,747,166 | 7/1973 | Eross | 24/81 |
| 4,109,888 | 8/1978 | Hayes | 248/443 |
| 4,115,966 | 9/1978 | DeLee | 52/148 |
| 4,211,380 | 7/1980 | Lillegard et al. | 248/229 |
| 4,321,992 | 3/1982 | Gallo | 192/81 |
| 4,547,092 | 10/1985 | Vetter et al. | 248/229 X |
| 4,666,111 | 5/1987 | Schuler | 248/125 |
| 4,674,722 | 6/1987 | Danby et al. | 248/231.3 |
| 4,706,368 | 11/1987 | Crissman, III et al. | 29/526 |
| 4,832,294 | 5/1989 | Eidem | 248/125 |
| 5,174,533 | 12/1992 | Pryor et al. | 248/231.7 X |

*Primary Examiner*—Eugenia Jones
*Assistant Examiner*—Raymond D. Woods
*Attorney, Agent, or Firm*—Workman Nydegger Jensen

[57] ABSTRACT

A universal mounting system for attaching any of a variety of I.V. devices to an I.V. pole. The mounting system has both a C-clamp and a spring-actuated clamp. The C-clamp attaches to the I.V. pole with a threaded stud that is manually adjustable with a knob. The spring-actuated clamp secures the I.V. device and is pivotally connected to the C-clamp by a pivot-screw that extends through both a spring and a non-threaded bore that is formed in the C-clamp, and exits at a recess area on the C-clamp. The pivot-screw is threaded into a threaded bore that extends through a projection on the spring-actuated clamp. The projection fits within the recess to prevent pivoting of the spring-actuated clamp relative to the C-clamp. The spring-actuated clamp has two aligned, opposing and spring-loaded clips for holding I.V. devices. The clips pivot and fulcrum together at a pivot point between the ends of each clip so as to bring the clip ends together to a clamped position on an I.V. device.

14 Claims, 4 Drawing Sheets

UNIVERSAL I.V. STAND MOUNTING SYSTEM

BACKGROUND

1. Field of the Invention

The present invention relates to an apparatus for attaching devices to a stand (hereinafter "I.V. stand") used for supporting various types of bags or bottles holding liquids for intravenous delivery to a patient. More particularly, the present invention relates to a universal mounting system which allows for quick, one-handed attachment and release of various I.V. devices to an I.V. pole, where the I.V. pole may be of varying configurations, including different sizes, shapes and orientations.

2. Background Art

One of the more basic tools used in a medical environment is an I.V. stand. The typical I.V. stand is comprised of an elongated member, or pole, which may be oriented either vertically or horizontally, and may additionally have any one of a variety of cross-sectional geometric shapes, including round, hexagonal or square. The pole is placed upon and supported by a base plate or pedestal. Typically, I.V. devices such as supply bags or bottles of an I.V. liquid—normally blood, saline solution, or medication—are attached to the I.V. pole. These liquids are then delivered via a thin tube to a patient who is in a bed adjacent the I.V. stand.

As medical technologies and treatment techniques have advanced, there are an increasingly large number of I.V. liquids that must be delivered to a patient. As such, there are often additional devices that must be attached to the I.V. stand to manage, control, measure, and/or monitor the delivery of these various liquids. One such device is referred to as a manifold which provides for the selective intravenous delivery of any one of a variety of fluids to a patient through a single delivery tube. Another such device is known as a multi-catheter organizer. This device is designed to attach to an I.V. stand and allow for the attachment of numerous catheter tubes in a collective and orderly fashion.

In order to minimize equipment costs and increase flexibility of use, these devices are typically required to be adaptable for use with various types of I.V. stands. In recognition of this, such devices have typically been mounted on an I.V. pole by way of a clamping assembly. However, there are several disadvantages inherent in the currently available clamping assemblies.

Often, these clamping assemblies are capable of attachment to the I.V. stand in only one position. Thus they may not be used interchangeably between a horizontally disposed I.V. pole and a vertically disposed I.V. pole. Similarly, these clamping assemblies are often limited as to the size and/or shape of the I.V. pole to which they can attach. While a clamp on a clamping assembly may be capable of attaching to a round I.V. pole, it may not be capable of attaching to a hexagonal, or square shaped pole. Similarly, these clamps are often limited to specific widths or diameters of poles to which they can properly attach. Each of these limitations restricts the adaptability and limits the usefulness of the clamping assembly.

Another and more substantial drawback of the currently available clamping assemblies is the inability to quickly attach and detach the various types of devices to the I.V. stand. Typically, these clamping assemblies utilize a "U" or C-shaped rigid clamping member in conjunction with a clamping screw that must be tightened or loosened by hand in order to clamp, or unclamp such a device as a manifold, catheter organizer or the like to an I.V. pole. The disadvantage of this configuration is the inherent difficulty of being able to quickly and firmly attach a device to the I.V. pole. Medical personnel are often required to quickly remove and attach various kinds of devices to an I.V. pole, especially in a hurried medical situation. The current clamping assemblies require an undue amount of time and difficulty to operate them. With clamping assemblies common in the prior art, a user must use both hands, one to grasp the clamp or pole while loosening or tightening the clamp's bolt or screw with the other hand, which proves to be slow and cumbersome. Also, it is difficult to hang an I.V. device, such as a catheter organizer, and attach it to or remove it from an I.V. stand while at the same time adjusting the clamping assembly's bolt. Often, this will undesirably result in the catheter organizer, or similar I.V. device, being dropped on the ground.

An additional disadvantage to clamping assemblies currently in use is that how securely a device is held is entirely dependent on the user sufficiently tightening the clamping bolt. Insufficient tightening may result in the device falling off the I.V. stand. Over-tightening results in adding difficulty when subsequently untightening to remove the device, and may even result in damage to the device, which is often constructed out of plastic materials.

OBJECTS OF THE INVENTION

It is, therefore, a primary object of the present invention to provide a universal mounting system for more quickly and securely attaching any of a variety of different attaching devices to an I.V. pole.

It is an additional object of the present invention to provide a universal mounting system that is easily and quickly adaptable for use on I.V. poles having different sizes and shapes.

It is also an object of the present invention to provide a universal mounting system that may function on both horizontally and vertically disposed I.V. poles by allowing the user to selectively rotate and lock the clamping assembly relative to the I.V. pole.

It is a further objective to advance the art to provide a universal mounting system that allows a user to quickly attach and detach various types of devices to an I.V. stand with only one hand, thus allowing the user to simultaneously grasp the device with the other hand.

It is a still further object of the present invention to provide a mounting system which, while still allowing for one-handed release and attachment of various types of devices, will clamp onto and hold such devices with sufficient force to prevent the devices from falling off.

It is yet another object of the present invention to provide a universal mounting system that incorporates a unique set of channel shaped jaws that correspond and clamp on to channel shaped brackets used on a variety of standard devices.

Other objects and advantages of the present invention are realized in the universal mounting system disclosed herein, and will become more fully apparent from the following detailed description and appended claims, or by practice of the invention.

BRIEF SUMMARY OF THE INVENTION

The present invention is directed to a universal mounting system for attaching a variety of different types of devices to an I.V. pole. The mounting system includes a novel combination of two clamping devices. The first clamp releasably attaches to an I.V. pole, and the second clamp releasably attaches to various types of I.V. devices.

In a preferred embodiment of the invention, the first clamp is a C-clamp, which has a generally open configuration allowing it to fully envelop an I.V. pole. A threaded bore is fashioned through one arm of the C-clamp through which a threaded stud may be extended or retracted by a hand knob, thus clamping or unclamping the I.V. pole.

The second clamp is pivotally connected to the first clamp such that the second clamp can be rotated and locked with respect to both the first clamp and the I.V. pole. In a preferred embodiment the second clamp may be locked in a position that is either parallel or normal to the I.V. pole.

In the preferred embodiment of the invention, I.V. devices are clamped and held by the second clamp by a pair of spring-loaded jaws that are manually operated with a single hand by applying pressure on the opposite ends of the spring-loaded jaws. The spring-loaded jaws are then released and permitted to close upon the I.V. device that is to be attached to the I.V. pole. This second clamp thus allows for a quick, one-handed attachment or release of the I.V. device.

The jaws used in the second clamp are preferably fashioned so as to form a channel-shaped enclosure at their ends. This channel shaped enclosure is intended to be able to enclose and clamp onto a similarly shaped channel typically found on many standard I.V. devices in current use, including the aforementioned multi-catheter organizer device or catheter manifold device.

BRIEF DESCRIPTION OF THE DRAWINGS

Reference is next made to a brief description of the drawings, which are intended to illustrate the preferred embodiment of the present invention with respect to the manner of making and using same in its presently understood best mode. The drawings and the detailed description which follow are intended to be merely illustrative and not otherwise limiting of the scope of the invention as set forth in the appended claims.

DETAILED DESCRIPTION OF THE PREFERRED EMBODIMENTS

Figure 1:
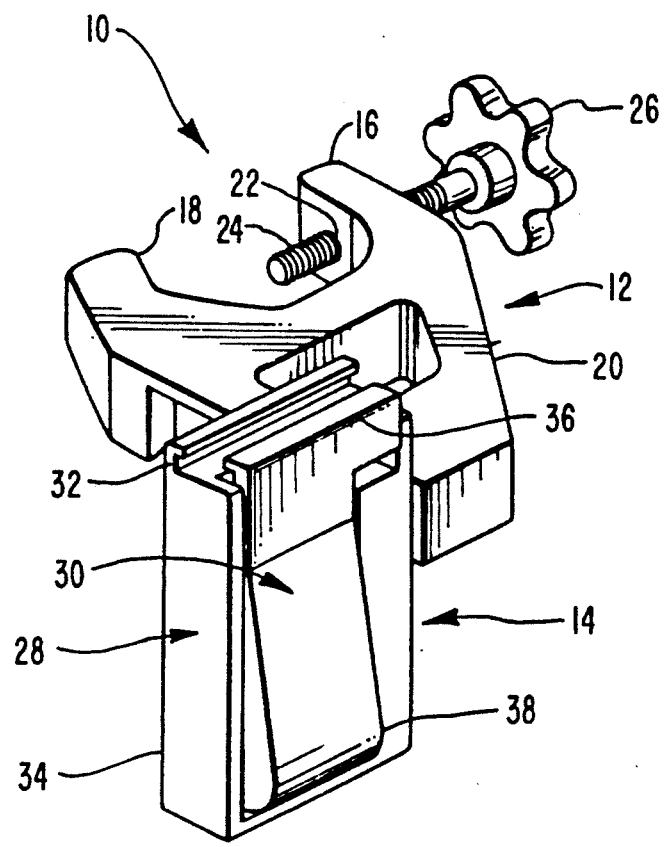
FIGS. 1 through 4 show various perspective views of the universal mounting system in various pivotal positions between the first and second clamping means.

Reference is now made to the drawings wherein like parts are designated with like numerals throughout. Referring first to FIG. 1, one presently preferred embodiment of the present invention is illustrated and designated generally at 10.

The mounting system 10 includes a first clamping means, as for example a C-clamp 12, and a second clamping means, as for example a spring-actuated clamp which is designated generally at 14. In a preferred embodiment, the C-clamp 12 is configured with two arms, 16 and 18, which together form a general C-shape with the body 20 of the C-clamp 12. A first arm 16 of the C-clamp has an internally threaded bore 22 through which extends a threaded stud 24. Attached at one end of the stud 24 is a knob 26 which permits easy adjustment of the stud 24 with the fingers of one hand. Thus, in operation the C-clamp arms 16, 18 are enveloped about an elongated member, such as a pole, and the hand knob 26 is then tightened so as to urge the stud 24 against the pole and clamp it against the second arm 18, such operation being illustrated in FIGS. 3 through 5 and 7.

Figure 6:
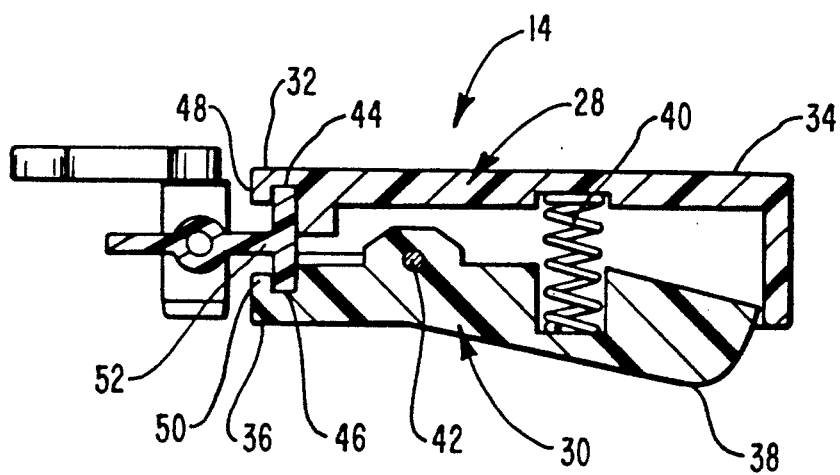
FIG. 6 is a cross-sectional view of the second clamping means taken along the 6—6 line in FIG. 5.

With continued reference to FIG. 1, the spring-actuated clamp 14 is configured with two clips 28 and 30, which are also shown in cross-section in FIG. 6. The first clip 28 has a jaw end 32 and a lever end 34. Similarly, the second clip 30 has a correspondingly shaped jaw end 36 and a lever end 38. The second clip 30 is partially disposed within the body of the first clip 28 such that the two jaw ends 32 and 36 are in an opposed, but non-contacting relationship, which is best seen in the cross-sectional view in FIG. 6.

With reference now to FIG. 6, it is illustrated now the clamp 14 has a spring 40 which is disposed between the first clip 28 and the second clip 30. The two clips 28, 30 are fulcrumed together at a pivot-pin 42 such that the spring 40 urges the jaw ends 32, 36 of the resilient clamp 14 into a substantially together or closed position. Thus, in operation a user may apply pressure with the fingers of one hand to the respective lever ends 34, 38 of the resilient clamp 14, so that the respective jaw ends 32, 36 may be urged apart, and into an open position prior to clamping a device.

Figure 5:
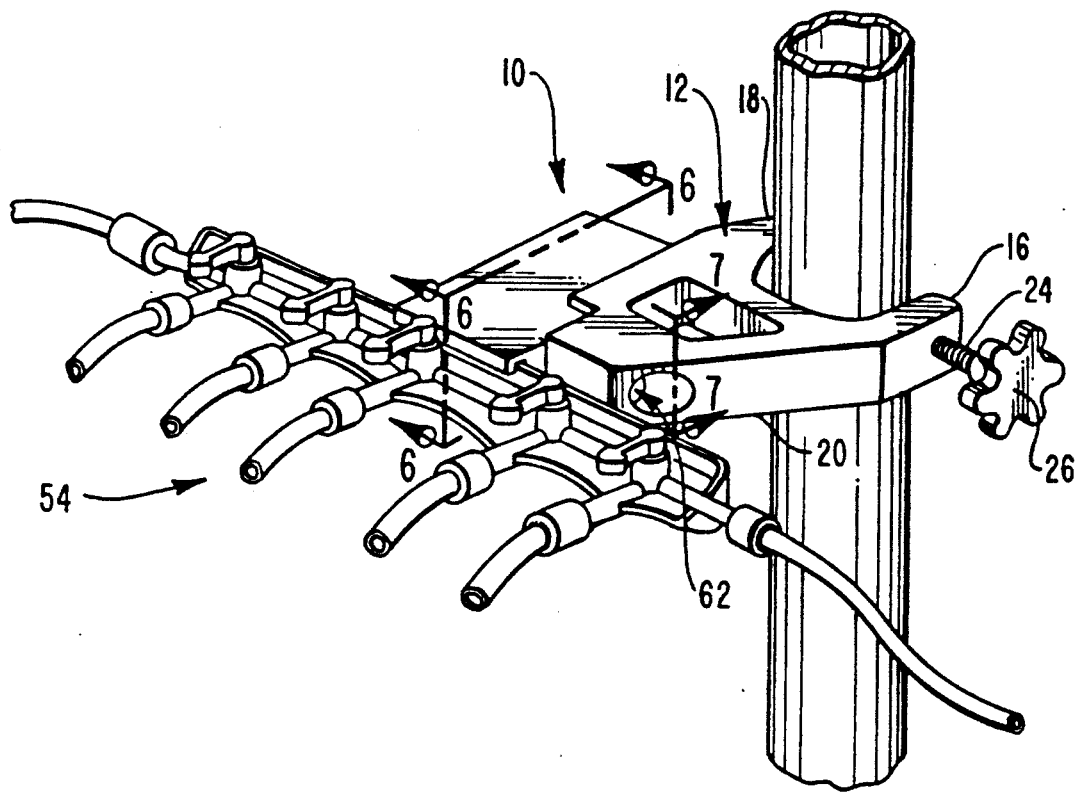
FIG. 5 is a perspective view of a universal mounting system releasably attached to an I.V. device such as a manifold.

With continued reference to FIG. 6, it is further illustrated how the opposing jaw ends 32, 36 of the resilient clamp 14 together form a channel shaped enclosure when they are in the closed position. Each jaw end 32, 36 has a continuous elongate rectangular groove 44, 46 formed along the inside lateral edge. Each lateral edge of the jaw end 32, 36 also has a projecting flange portion 48, 50 which projects normal to the lateral edge of the jaw and in a direction towards the opposing clip. The resulting channel-shaped enclosure is designed such that it may clamp a T-shaped bracket 52 (shown in cross-section in FIG. 6) that is standard on many I.V. devices. One such device is a catheter manifold 54, which is shown in FIG. 5 clamped by the present universal mounting system 10.

Figure 7:
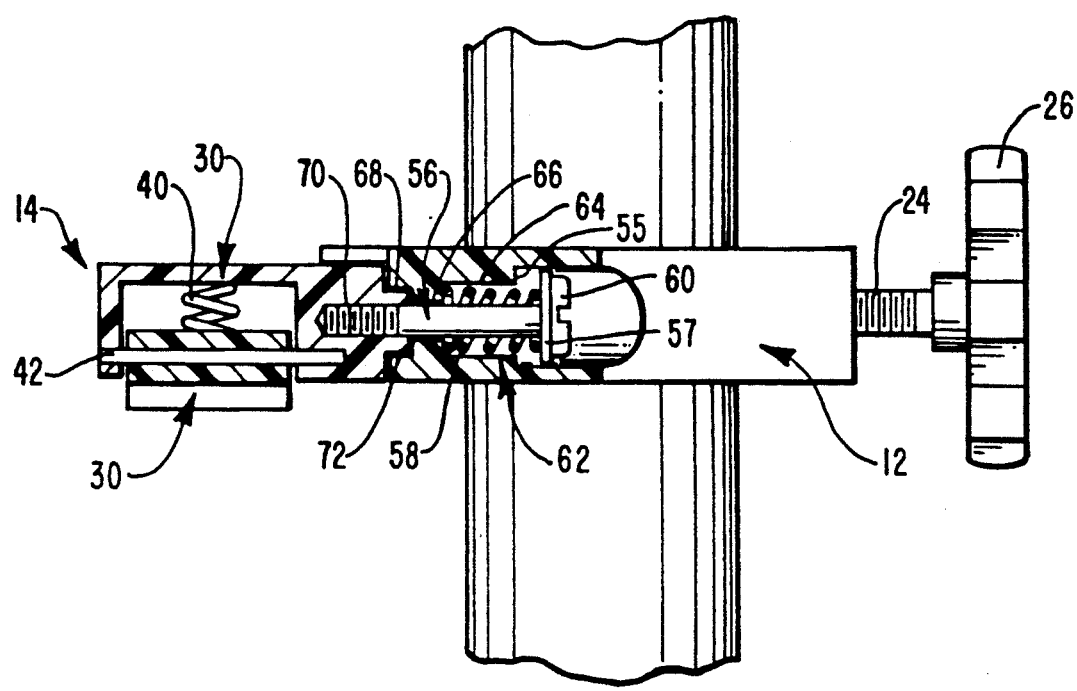
FIG. 7 is a cross-sectional view of the pivot lock mechanism taken along the 7—7 line in FIG. 5.
Figure 8:
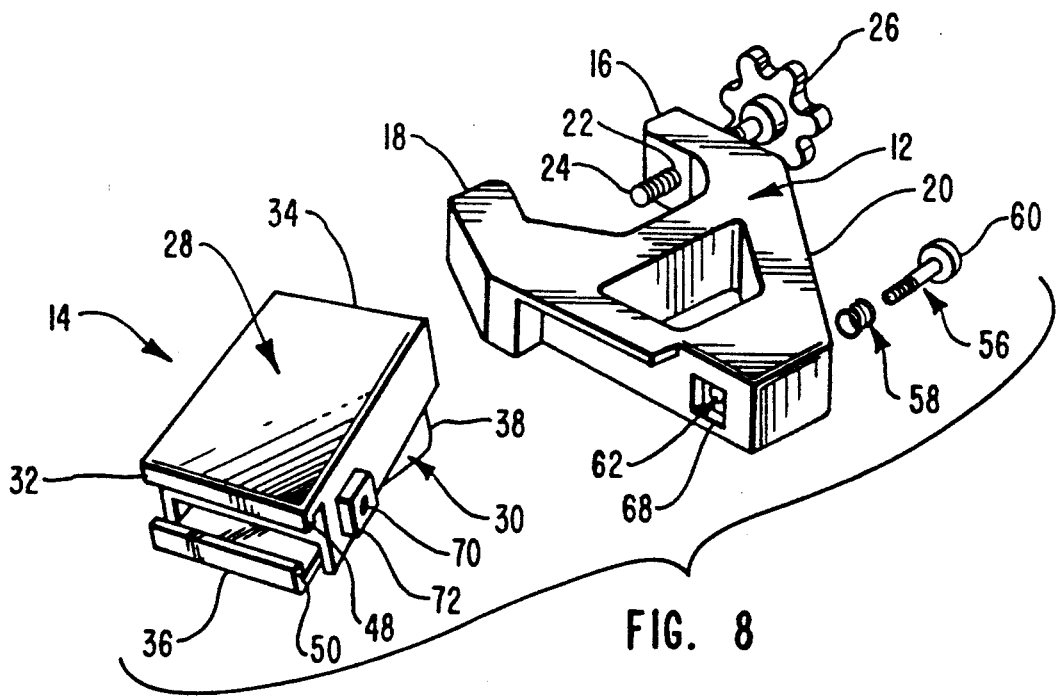
FIG. 8 is an exploded perspective view of the universal mounting system.

The resilient clamp 14 is pivotally connected to the C-clamp 12, and in operation may be rotated and locked in different positions relative to the C-clamp 12. This is accomplished by a releasable locking means, or locking mechanism, which is comprised, by way of example, of several elements that are best seen in FIGS. 7 and 8. FIG. 8 illustrates a pivot-screw 56, which has a screw head 60 at one end and is threaded at the opposite end, and also illustrates a spring 58, which is coiled around the pivot-screw, but has a diameter that is less than the diameter of a washer 57 and screw head 60. With the spring 58 coiled around a portion of the length of the pivot-screw 56, it is extended through a non-threaded bore 62 which is formed through the body of the C-clamp 20. The non-threaded bore 62 is made up of three portions, each of which have different cross-sectional characteristics.

Referring now to the cross-sectional view of FIG. 7, the first portion 64 of the non-threaded bore 62 enters a lateral edge of the C-clamp and has a diameter that is smaller than that of both the screw head 60 and the washer 57. A second portion 66 of the non-threaded bore 62 has a diameter that may slideably receive the length of the pivot-screw 56, but that is smaller then the diameter of the washer 57 and of the spring 58. The third portion of the non-threaded bore 62 exits at a opposite lateral side of the C-clamp 12 as a recessed area 68. This recessed area 68 is preferably formed as a tapered cube or polygonal shape.

With continued reference to FIG. 7, the pivot-screw 56 exits the recessed area 68 and is threadably engaged with a second threaded bore 70 that extends through a locking member projection 72, which is formed on a lateral edge of the first clip 28 of the spring-actuated clamp 14. The projection 72 is formed into a shape that conforms to the shape formed in the recessed area 68, preferably a tapered cube with four equal transverse sides such that the locking member projection 72 is able to be received in a sliding and tight fitting relationship with the recessed area 68. This tight fitting and conformal relationship is best seen in the cross-sectional view shown in FIG. 7. The slight taper of projection 72 allows for easy entry into the recessed area 68.

With continued reference to FIG. 7, it is illustrated how the locking mechanism locks the resilient clamp 14 with respect to the C-clamp 12. The spring 58 exerts a constant force on the pivot-screw 56 via the washer 57 which abuts shoulder 55, which in turn urges and maintains the locking member projection 72 into the tight fitting and conformal relationship within the recessed area 68. In such a position, the resilient clamp 14 is locked and may not rotate with respect to the C-clamp 12.

Figure 2:
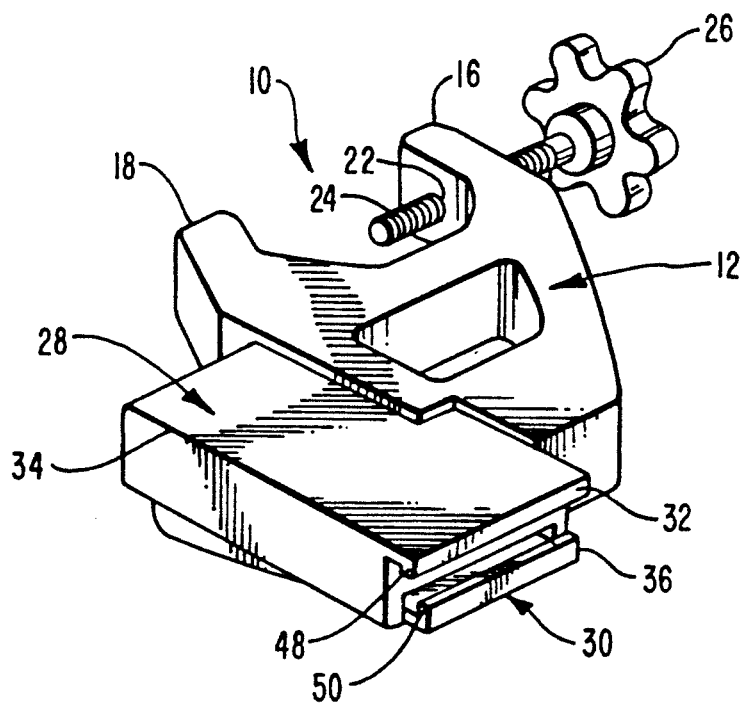
Figure 3:
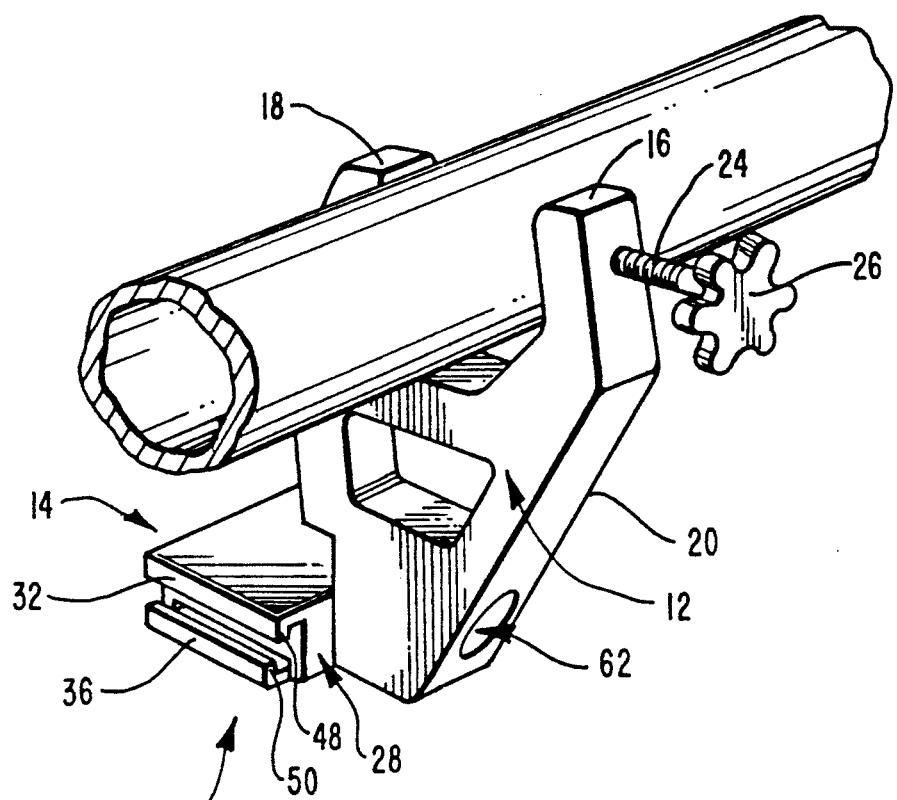
Figure 4:
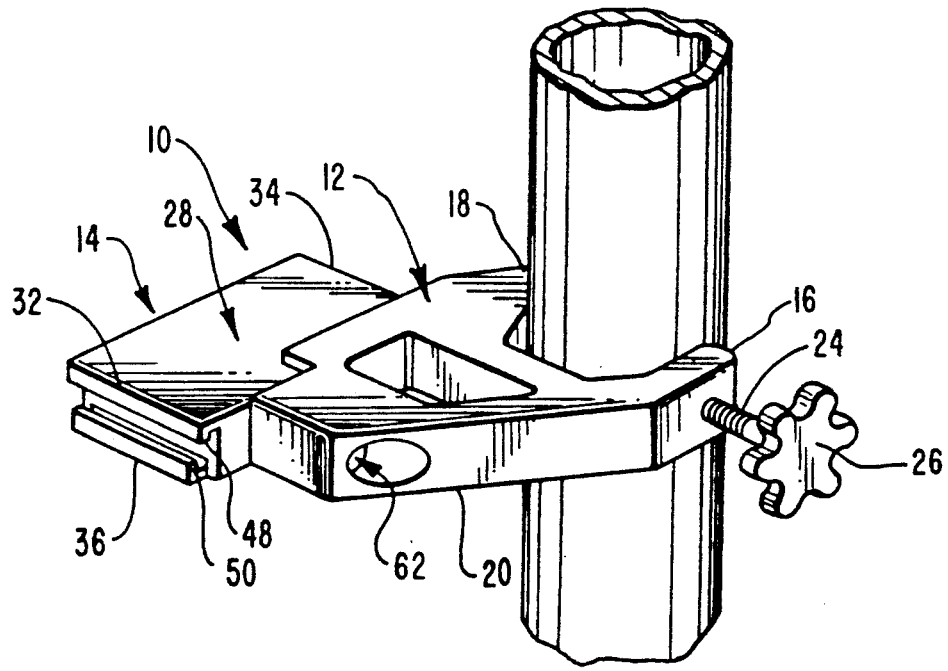

In order to rotate the resilient clamp 14 relative to the C-clamp 12, a user must pull on the resilient clamp 14 in a direction parallel with the pivot-screw 56 with a force sufficient to overcome the opposing force exerted by the spring 58. The resilient clamp 14 is then separated from the C-clamp 12 such that the locking member projection 72 is no longer seated within the recessed area 68. The user then pivots the resilient clamp 14 to a point where the locking member projection 72 is not geometrically aligned with the recessed area 68, at which point the pulling force may be stopped. The user continues to rotate the resilient clamp 14 about the pivot screw 56 until the locking member projection 72 is again geometrically aligned with the recessed area 68. At this point, the spring 58 will quickly snap the locking member projection back in to a tight fitting and conformal relationship with the recessed area 68 where the resilient clamp 14 will again be in the locked position relative to the C-clamp 12. In the preferred embodiment, the locking member projection 72 and the recessed area 68 are formed into a tapered cube shape, whereby the resilient clamp 14 can be rotated ninety degrees between locked positions. Thus, the resilient clamp 14 may be in a position that is normal to the C-clamp 12, as is illustrated in FIGS. 1 and 3, or in a position parallel to the C-clamp 12, as is illustrated in FIGS. 2 and 4. It will be appreciated however, that other polygonal shapes could be used to provide a plurality of different, angularly oriented locking positions and such shapes and all equivalents thereof are considered to be within the scope of the presently disclosed invention.

In the preferred embodiment, when the spring 58 urges the locking member projection 72 into the tight fitting and conformal relationship within recess 68, the impact of the conforming surfaces onto each other will result in an audible "snap" which will inform the user that the resilient clamp 14 is now locked with respect to the C-clamp 12.

It will be appreciated by one skilled in the relevant art that a universal mounting system according to the present invention may be made of a variety of materials. However, it is presently preferred that the mounting system be made of a lightweight metal, such as aluminum. Thus, the system will have improved structural rigidity.

It will be appreciated that the apparatus of the present invention is capable of being incorporated in the form of a variety of embodiments. The invention may thus be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. Universal mounting system for attaching an I.V. device to an elongated member, comprising:
   a first clamping means for clamping to said elongated member; and
   a second clamping means, pivotally connected to said first clamping means for applying a releasable clamping force to said I.V. device thereby holding said I.V. device in a firm yet releasable manner, said second clamping means comprising a spring-biased releasable locking means for both selectively positioning and locking said second clamping means relative to said first clamping means, said releasable locking means comprising in combination a polygonally shaped recess formed on one of said first and second clamping means and a correspondingly shaped locking member projecting from the other of the first and second clamping means, and wherein the recess and locking member fit together in a tight fitting, conformal relationship in any one of a plurality f pivotal orientations at predetermined angles defined by the polygonal shape of the recess.

2. A universal mounting system as defined in claim 1, wherein said first clamping means comprises:
   a C-shaped element having a first and a second arm, and a threaded stud having a distal and a proximal end, said threaded stud proximal end having a knob, said threaded stud having external threads between said proximal and distal ends for threadably engaging an internally threaded bore formed through said first arm, whereby the first and second arms of said C-shaped element at least partially surround said elongated member, and the threaded stud manually adjusts with said knob so as to bear the threaded stud distal end against the elongated member to both urge and clamp the elongated member against the second arm.

3. A universal mounting system as defined in claim 1, wherein said second clamping means further comprises a first and a second clip, each said first and second clip having a jaw end and an opposite lever end and being aligned in an opposing relationship and being fulcrumed together at a pivot point between respective jaw and lever ends and further having a biasing means for pivoting the first and second clips about said pivot point with a biasing force, whereby said biasing force brings said jaw ends together to a substantially closed and clamped position, and whereby oppositely directed forces applied to said lever ends being greater than said biasing force will cause the clips to pivot about said pivot point to separate the jaw ends to a substantially open and unclamped position.

4. A universal mounting system as defined in claim 3, wherein said jaw ends form a channel shape in said closed and clamped position comprising:
a continuous elongate rectangular groove adjacent to a lateral edge on each said jaw end, each said jaw end lateral edge having a projecting flange portion, each said projecting flange portion being normal toe ah said jaw end lateral edge and being oriented in a direction towards the projecting flange portion of the opposing jaw end and being adjacent to said continuous elongate rectangular groove, whereby the channel-shaped jaw ends clamp onto a T-shaped bracket on said I.V. device when the first and second clips are in said substantially closed and clamped position.

5. A universal mounting system as defined in claim 1, wherein said releasable locking means is further comprised of a pivot-screw and a spring, the pivot-screw having a distal end that is threaded and a proximal end that terminates at a screw head having a predetermined first width, the spring having a predetermined second width so as to receive said pivot-screw and disposed between the pivot-screw distal and proximate ends, the pivot-screw being fully extended through a non-threaded bore fashioned through the first clamping means, said non-threaded bore having a first and a second length, said first length entering a first lateral edge of said first clamping means and having a width larger then the first width of said screw head, and said second length having a width smaller than the first width of the screw head and the second width of the spring, said non-threaded bore exiting at a second lateral edge of said first clamping means at one of the recess and the locking member, said threaded distal end of said pivot-screw exiting the non-threaded bore and being threadably engaged with a second threaded bore fashioned through the second clamping means, said second threaded bore extending through the other of the recess and the locking member on the second clamping means.

6. A universal mounting system as defined in claim 5, wherein said spring exerts a continuously opposed biasing force to the screw head and to the first clamping means so as to maintain the locking member in said tight fitting and nonformal relationship within said recess, and whereby said first clamping means is pivoted and locked relative to said second clamping means by removing said locking member from said recess by applying a continuous pulling force to the second clamping means in a direction away from said first clamping means, said pulling force being directed parallel to the longitudinal axis of said pivot-screw, and pivoting said second clamping means relative to said first clamping means until said locking member is in a next geometric alignment position with said recess, and reducing the continuous pulling force to insert said locking member within said recess, said locking member being urged into said tight fitting and conformal relationship within said recess by said opposed biasing force, such that the recessed area and' said locking member make an impact together so as to result in an audible click.

7. A universal mounting system for attaching an I.V. device to an I.V. pole, comprising:
a first clamping means for releasably clamping to said pole;
a second clamping means, connected in a pivotal orientation to said first clamping means, for releasably clamping to said device, said second clamping means comprising:
a first and a second clip, said first and second clips each having a jaw end and a lever end and being aligned in an opposing relationship and being fulcrumed together at a pivot point between respective jaw and lever ends and further having a biasing means for pivoting the first and second clips about said pivot point with a biasing force, whereby said biasing force brings said jaw ends together to a substantially closed and clamped position, and whereby oppositely directed forces applied to said lever ends being greater than said biasing force causes the clips to pivot about said pivot point to separate the jaw ends to a substantially open and unclamped position; and
a releasable locking means for selectively positioning and locking the pivotal orientation of said second clamping means in any one of a plurality of positions relative to said first clamping means.

8. A universal mounting system as defined in claim 7, wherein said first clamping means comprises:
a C-shaped element having a first and a second arm, and a threaded stud having a distal and a proximal end, said threaded stud proximal end having a knob, said threaded stud having external threads between said proximal and distal ends and threadably engaging an internally threaded bore formed through said first arm, whereby the first and second arms of said C-shaped element at least partially surround said I.V. pole, and the threaded stud manually adjusts with said knob so as to bear the threaded stud distal end against the I.V. pole to both urge and clamp the I.V. pole against the second arm.

9. A universal mounting system as defined in claim 8, wherein said releasable locking means is further comprised of a pivot-screw and a spring, the pivot-screw having a distal end that is threaded and a proximal end that terminates at a screw head having a predetermined first width, the spring having a predetermined second width so as to receive said pivot screw and be disposed between the pivot-screw distal and proximal ends, the pivot-screw being fully extended through a non-threaded bore fashioned through the first clamping means, said non-threaded bore having a first and a second length, said first length entering a first lateral edge of said first clamping means and having a width larger than the first width of said screw head, and said second length having a width smaller than the first width of the screw head and the second width of the spring, said nonthreaded bore exiting at a second lateral edge of said first clamping means at a recessed area formed thereon, said threaded distal end of said pivot-screw exiting the non-threaded bore at said recessed area and being threadably engaged with a second threaded bore fashioned through the second clamping means, said second threaded bore extending through a locking member projecting from the second clamping means.

10. A universal mounting system as defined in claim 9, wherein said jaw ends form a channel shape in said closed and clamped position comprising:

a continuous elongate rectangular groove adjacent to a lateral edge on each said jaw end, each said jaw end lateral edge having a projecting flange portion, each said projecting flange portion being normal to each said jaw end lateral edge and being oriented in a direction towards the projecting flange portion of the opposing jaw end and being adjacent to said continuous elongate rectangular groove, whereby the channel-shaped jaw ends clamp onto a T-shaped bracket on said device when the first and second clips are in said substantially closed and clamped position.

11. A universal mounting system as defined in claim 10, wherein said recessed area is recessed into a specific geometric shape which is able to be in a tight fitting and conformal relationship with said locking member, aid locking member being slideably receivable within said recessed area, whereby said tight fitting and conformal relationship fixed the second clamping means in a non-pivotal and locked position relative to the first clamping means.

12. A universal mounting system as defined in claim 11, wherein said recessed area is formed as a polygonal shape.

13. A universal mounting system as defined in claim 12, wherein:

said spring exerts a continuously opposed biasing force both to the screw head and to the first clamping means so as to maintain the locking member in said tight fitting and conformal relationship within said recessed area, whereby said first clamping means is pivoted and locked relative to said second clamping means by removing said locking member from said recessed area by applying a continuous pulling force to the second clamping means in a direction away from said first clamping means, said pulling force being directed parallel to the longitudinal axis of said pivot-screw, and pivoting said second clamping means relative to said first clamping means until said locking member is in a next geometric alignment position with said recessed area, and reducing the continuous pulling force to insert said locking member within said recessed area, said locking member being urged into said tight fitting and conformal relationship within said recessed area by said opposed biasing force, such that the recessed area and said locking member make an impact together so as to result in an audible click.

14. A universal mounting system for attaching a device to an I.V. pole, comprising:

a C-clamp having a first and a second arm, and a threaded stud having a distal and a proximal end, said threaded stud proximal end having a knob, said threaded stud having external threads between said proximal and distal ends for threadably engaging an internally threaded bore formed through said first arm;

a spring-actuated clamp pivotally connected to aid C-clamp by a pivot-screw extending through both a spring and a non-threaded bore formed in the C-clamp, said pivot-screw exiting at a polygonal recess area on a lateral edge of said C-clamp and being threadably engaged with a second threaded bore extending through a correspondingly shaped polygonal locking member formed on a lateral edge of the spring-actuated clamp, said spring-actuated clamp further comprising:

a first and a second clip, each said first and second clip having a jaw end and an opposite lever end and being aligned in an opposing relationship and being fulcrumed together at a pivot point between respective jaw and lever ends and further having a biasing means for pivoting the first and second clips about said pivot point with a biasing force to bring said jaw ends together in a substantially closed and clamped position; and wherein the jaw ends form a channel shape in said closed and clamped position comprising a continuous elongate rectangular groove adjacent to a lateral edge on each said jaw end, each said jaw end lateral edge having a projecting flange portion, each said projecting flange portion being normal to each said jaw end lateral edge and being oriented in a direction towards the projecting flange portion of the opposing jaw end and being adjacent to said continuous elongate rectangular groove, whereby the channel-shaped jaw ends clamp onto said device when the first and second clips are in said substantially closed and clamped position.

* * * * *

UNITED STATES PATENT AND TRADEMARK OFFICE
CERTIFICATE OF CORRECTION

PATENT NO. : 5,322,253
DATED : June 21, 1994
INVENTOR(S) : BRIAN STEVENS

It is certified that error appears in the above-indentified patent and that said Letters Patent is hereby corrected as shown below:

```
Column 6, line 51, "f" should be --of--
Column 7, line 23, "toe ah" should be --to each--
Column 7, line 59, "nonformal" should be --conformal--
Column 8, line 6, "recessed area" should be --recess--
Column 9, line 23, "aid" should be --said--
Column 9, line 26, "fixed" should be --fixes--
Column 10, line 16, "aid" should be --said--
```

Signed and Sealed this

Twenty-ninth Day of November, 1994

Attest:

BRUCE LEHMAN

*Attesting Officer*   *Commissioner of Patents and Trademarks*